United States Patent
Houde et al.

(10) Patent No.: US 9,737,363 B2
(45) Date of Patent: Aug. 22, 2017

(54) STERILE DRAPE FOR TWO TIERED HOSPITAL INSTRUMENT TABLE

(71) Applicant: AVENT, INC., Alpharetta, GA (US)

(72) Inventors: Ajay Y. Houde, Duluth, GA (US); Jeffrey S. Robinson, Marietta, GA (US); Jose Luis Coronado, Tuscon, AZ (US); Keith J. Edgett, Middletown, DE (US); James B. Robinson, Cumming, GA (US); Denise E. O'Connor, Philadelphia, PA (US)

(73) Assignee: Avent, Inc., Alpharetta, GA (US)

(*) Notice: Subject to any disclaimer, the term of this patent is extended or adjusted under 35 U.S.C. 154(b) by 500 days.

(21) Appl. No.: 13/710,568

(22) Filed: Dec. 11, 2012

(65) Prior Publication Data

US 2014/0041669 A1     Feb. 13, 2014

Related U.S. Application Data

(60) Provisional application No. 61/681,846, filed on Aug. 10, 2012, provisional application No. 61/715,974, filed on Oct. 19, 2012.

(51) Int. Cl.
*A61B 19/08*     (2006.01)
*A61B 50/13*     (2016.01)
(Continued)

(52) U.S. Cl.
CPC ............ *A61B 19/081* (2013.01); *A61B 46/00* (2016.02); *A61B 46/10* (2016.02); *A61B 46/40* (2016.02); *A61B 50/13* (2016.02); *A61B 50/15* (2016.02)

(58) Field of Classification Search
CPC ..... A61B 19/08; A61B 19/081; A61B 19/088; A61B 2019/025; A61B 2019/0251;
(Continued)

(56) References Cited

U.S. PATENT DOCUMENTS

| 3,557,856 A | 1/1971 | Berman |
| 3,727,272 A * | 4/1973 | Rhodes ................. A41H 15/00 24/300 |

(Continued)

FOREIGN PATENT DOCUMENTS

| DE | 39 13 617 A1 | 10/1990 |
| FR | 745004 A | 5/1933 |
| WO | WO 98/26923 | 6/1998 |

OTHER PUBLICATIONS

Fitzwater, Janet, "Bacteriological Effect of Ultraviolet Light on a Surgical Instrument Table," Public Health Reports, vol. 76, No. 2, Feb. 1961, pp. 97-104.
(Continued)

*Primary Examiner* — Kari Rodriquez
(74) *Attorney, Agent, or Firm* — Dority & Manning, P.A.

(57) ABSTRACT

The present disclosure describes a draping system for a two-tiered hospital instrument back table can be used to quickly and conveniently create a sterile field. The system has a drape that is a single piece of material, desirably a film that may be clear. The single piece of material has other material attached to it on its upper side or surface in areas that generally coincide with the two upper surfaces of the table when the drape is installed on the table, and that has a lower coefficient of friction than the single piece of material. The drape may be held in place with a continuous or discontinuous band that encircles the upper tier or the upper tier support posts.

16 Claims, 6 Drawing Sheets

(51) Int. Cl.
*A61B 50/15* (2016.01)
*A61B 46/00* (2016.01)
*A61B 46/10* (2016.01)

(58) Field of Classification Search
CPC .... A61B 2019/0255; A61B 2019/0259; A61B 46/10; A61B 46/40; A47C 21/026; A47C 21/022; A47C 31/10; A47C 31/105; A47C 31/11; A47G 21/167
See application file for complete search history.

(56) References Cited

U.S. PATENT DOCUMENTS

| | | | |
|---|---|---|---|
| 3,730,338 A | 5/1973 | Chesky | |
| 3,738,405 A | 6/1973 | Ericson | |
| 3,747,655 A | 7/1973 | Hadtke | |
| 3,791,382 A | 2/1974 | Collins | |
| 3,799,161 A | 3/1974 | Collins | |
| 3,834,756 A | 9/1974 | Grell | |
| 3,902,484 A | 9/1975 | Winters | |
| 3,991,912 A | 11/1976 | Soto | |
| 3,998,221 A | 12/1976 | Collins | |
| 4,040,418 A | 8/1977 | Collins | |
| 4,080,963 A | 3/1978 | Merry et al. | |
| 4,098,536 A | 7/1978 | Mills | |
| 4,119,093 A | 10/1978 | Goodman | |
| 4,164,941 A | 8/1979 | Knopick et al. | |
| 4,185,625 A | 1/1980 | Morris | |
| 4,196,723 A | 4/1980 | Moose, Jr. | |
| 4,354,486 A | 10/1982 | Oliver | |
| 4,471,769 A | 9/1984 | Lockhart | |
| 4,489,720 A | 12/1984 | Morris et al. | |
| 4,564,548 A | 1/1986 | Fast | |
| 4,574,796 A | 3/1986 | Lundstroem et al. | |
| 4,607,631 A | 8/1986 | Hanssen | |
| 4,627,363 A * | 12/1986 | Jones | A47B 13/086 |
| | | | 108/90 |
| 4,664,103 A | 5/1987 | Martin et al. | |
| 4,705,084 A * | 11/1987 | Rodebaugh | A47C 31/10 |
| | | | 108/90 |
| 4,873,997 A | 10/1989 | Marshall | |
| 4,948,154 A | 8/1990 | Guggenheim | |
| 4,976,274 A | 12/1990 | Hanssen | |
| 4,991,242 A | 2/1991 | Brown | |
| 5,151,314 A | 9/1992 | Brown | |
| 5,170,804 A | 12/1992 | Glassman | |
| 5,170,826 A | 12/1992 | Carstensen et al. | |
| 5,226,815 A | 7/1993 | Bowman | |
| 5,227,218 A | 7/1993 | Herum | |
| 5,299,582 A * | 4/1994 | Potts | A61F 13/00 |
| | | | 128/846 |
| 5,322,072 A | 6/1994 | Harrison et al. | |
| 5,341,821 A | 8/1994 | DeHart | |
| 5,349,967 A | 9/1994 | Tennis et al. | |
| 5,379,703 A | 1/1995 | Marshall | |
| 5,411,036 A | 5/1995 | Wilkes | |
| 5,429,142 A | 7/1995 | Szabo et al. | |
| 5,435,322 A | 7/1995 | Marshall | |
| 5,503,163 A | 4/1996 | Boyd | |
| 5,538,012 A | 7/1996 | Wiedner et al. | |
| 5,546,961 A | 8/1996 | Harrison | |
| 5,560,974 A | 10/1996 | Langley | |
| 5,592,952 A | 1/1997 | Bohn | |
| 5,655,810 A | 8/1997 | Shikler | |
| 5,701,617 A | 12/1997 | Colby | |
| 5,704,370 A | 1/1998 | Gawarecki | |
| 5,766,737 A | 6/1998 | Willey et al. | |
| 5,816,253 A | 10/1998 | Sosebee | |
| 5,871,015 A | 2/1999 | Lofgren et al. | |
| 5,875,780 A | 3/1999 | Rodriguez | |
| 5,901,706 A * | 5/1999 | Griesbach | B32B 27/12 |
| | | | 128/849 |
| 5,938,304 A | 8/1999 | Irby et al. | |
| 6,019,102 A | 2/2000 | Becker | |
| 6,138,676 A | 10/2000 | Bruhn | |
| 6,286,162 B1 | 9/2001 | Huart | |
| 6,381,812 B1 * | 5/2002 | Crider | 24/289 |
| 6,497,233 B1 * | 12/2002 | DeAngelis | A61B 19/081 |
| | | | 128/849 |
| 2004/0194673 A1 | 10/2004 | Comeaux et al. | |

OTHER PUBLICATIONS

Modern Methods of Antiseptic Wound Treatment, published by Johnson & Johnson, 1891, 60 pages.

Nelson, J. Phillip et al., "Horizontal Flow Operating Room Clean Rooms," Clean Air Symposium—Part II, Cleveland Clinic Quarterly, vol. 40, No. 4, Winter 1973, pp. 191-202.

Schultz, Janet K. and the Professional Advisory Committee, "The Experts Research Q&A: Is the Underside of a Draped Mayo Sterile or Unsterile?" AORN Journal, vol. 33, No. 4, Mar. 1981, pp. 644-645.

SICO Room Service and Mobile Catering Tables brochure, SICO Incorporated, Minneapolis, MN, 1990, 4 pages.

* cited by examiner

STERILE DRAPE FOR TWO TIERED HOSPITAL INSTRUMENT TABLE

This application claims priority from U.S. provisional patent applications 61/681,846 filed on Aug. 10, 2012 and from 61/715,974 filed Oct. 19, 2012, respectively.

The present disclosure relates to sterile surface covers and more particularly to drapes for instrument tables in operating rooms.

In hospital operating rooms, areas that are sterile and non-sterile are carefully delineated. Typically a surface that is to hold instruments such as a metal table is covered by a sterile drape. The surface of the table itself is considered non-sterile, being made sterile by the application of a drape. Any area below the draped surface is also considered non-sterile.

A two tiered table is commonly used in hospital surgical suites and has one working tier surface arranged at standard table height and a second working tier surface arranged above the first. These types of table are known as surgical "back instrument tables" or more simply "back tables". The upper tier is generally of a lesser depth than the lower tier, though the widths are generally the same. Rather than attempt to sterilize the entire table, a drape as described in U.S. Pat. No. 6,019,102 was developed. This drape covers the table surfaces, but the drape fabric above the lower surface may sag toward the lower surface, particularly on either end of the table. In addition, it can slip off of the table onto the floor as it is being installed. If this occurs, the drape is no longer sterile and so a new drape must be used at additional cost.

There is a need for a drape that will not use a central fastening system and will make the drape better conform to the upper tier of the table. The drape will also desirably be less likely to slip onto the floor during installation.

SUMMARY

There is provided a draping system that addresses the issues mentioned above. The draping system has a drape that is a single piece of material, desirably a film that may be clear. The single piece of material may have other material attached to it on its upper side or surface in one or two areas that at least generally coincide with the two upper surfaces of the table when the drape is installed on the table, and that has a higher coefficient of friction than the single piece of material.

Most films have a relatively low coefficient of friction, so the single piece of material also desirably has a high coefficient of friction material attached to it on its lower side or surface in an area that coincides with at least the upper surface of the lower tier of the table when the drape is installed. There may be additional high coefficient of friction material attached to the lower side of the single piece of material in an area that generally coincides with the upper surface of the upper tier of the table.

The single piece material is desirably fitted so as to aid in avoiding impeding access to and visibility of the surfaces immediately beneath the upper tier. The draping system does not use (i.e. is free of) a hook and loop type fastener to fasten the center of the drape to the table. The draping system uses a band of continuous or discontinuous material to at least partially encircle the upper tier, or the upper area of the upper tier support posts. The draping system for the two-tiered hospital instrument back table can be used to quickly and conveniently create a sterile field.

DETAILED DESCRIPTION

Figure 1:
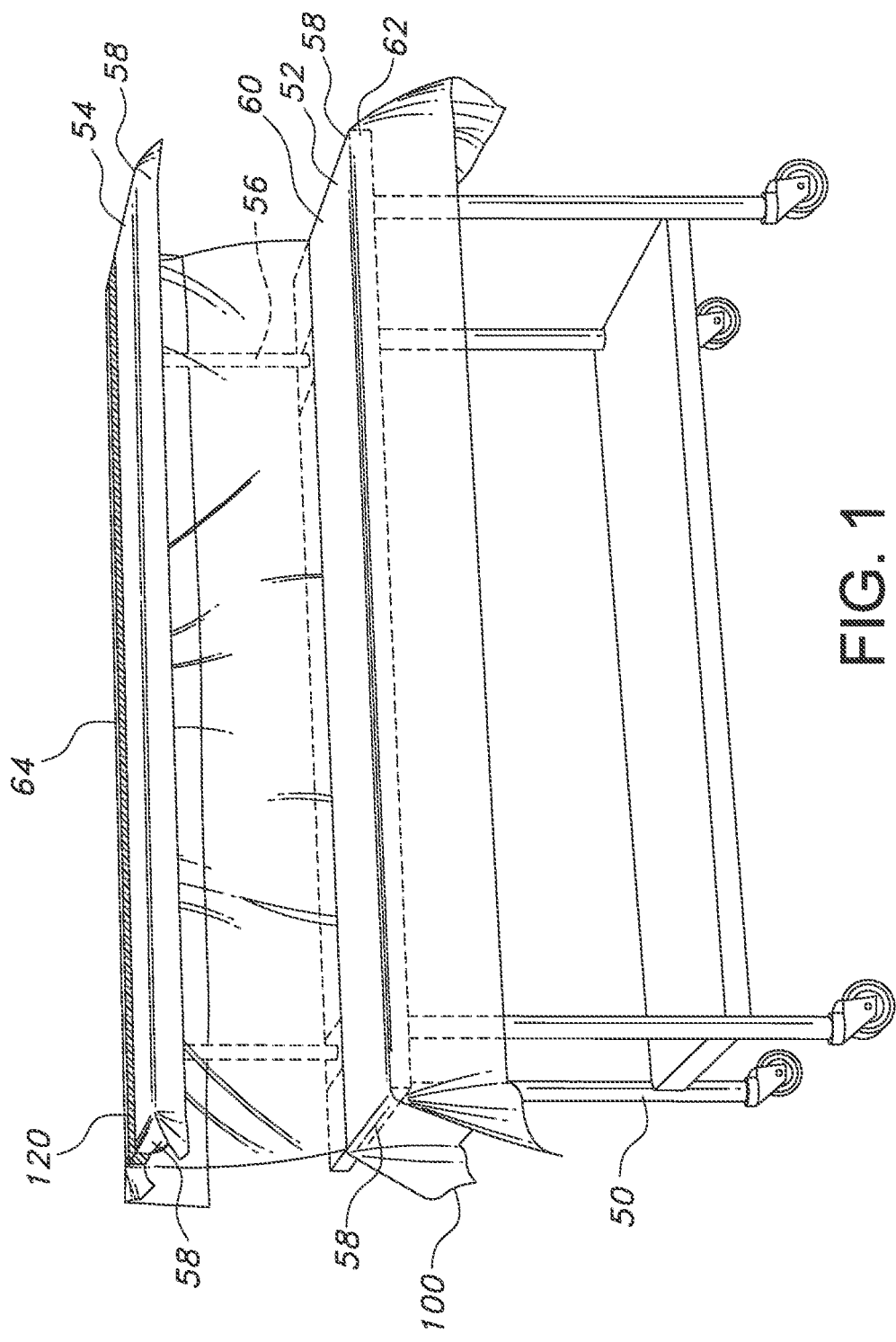
FIG. 1 is a perspective view of a surgical instrument table covered with the surgical sterile drape and held in place with a continuous band of elastic encircling the upper tier from end to end

As can be seen from FIG. 1, the back table 50 has a lower tier 52 and upper tier 54. The upper tier 54 is supported at the rear by at least two uprights or posts 56 near either end 58. Each tier has an upper surface 60 and a front 62, rear 64 and two ends 58. On some tables the tiers are adjustable in height and angle so they are not necessarily the same distance apart nor are they necessarily horizontal or parallel to each other.

Figures 2A, 2B:
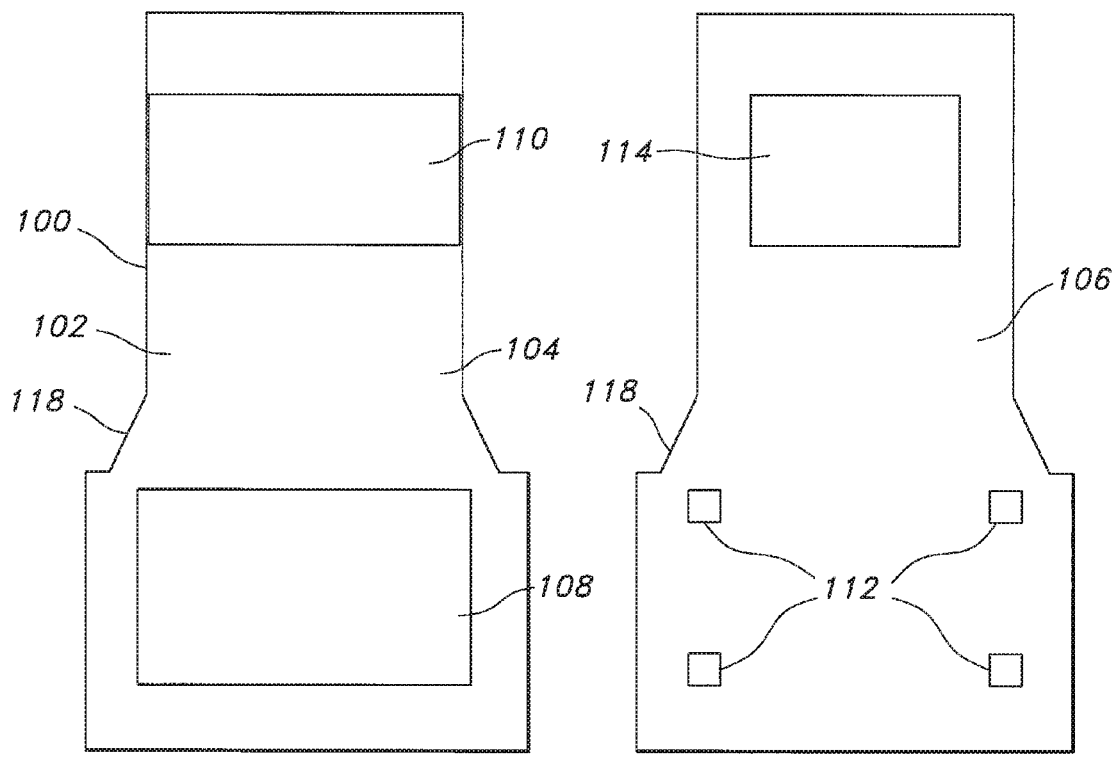
FIG. 2A-C are plan views of the one-piece embodiment of the surgical drape.
Figure 2C:
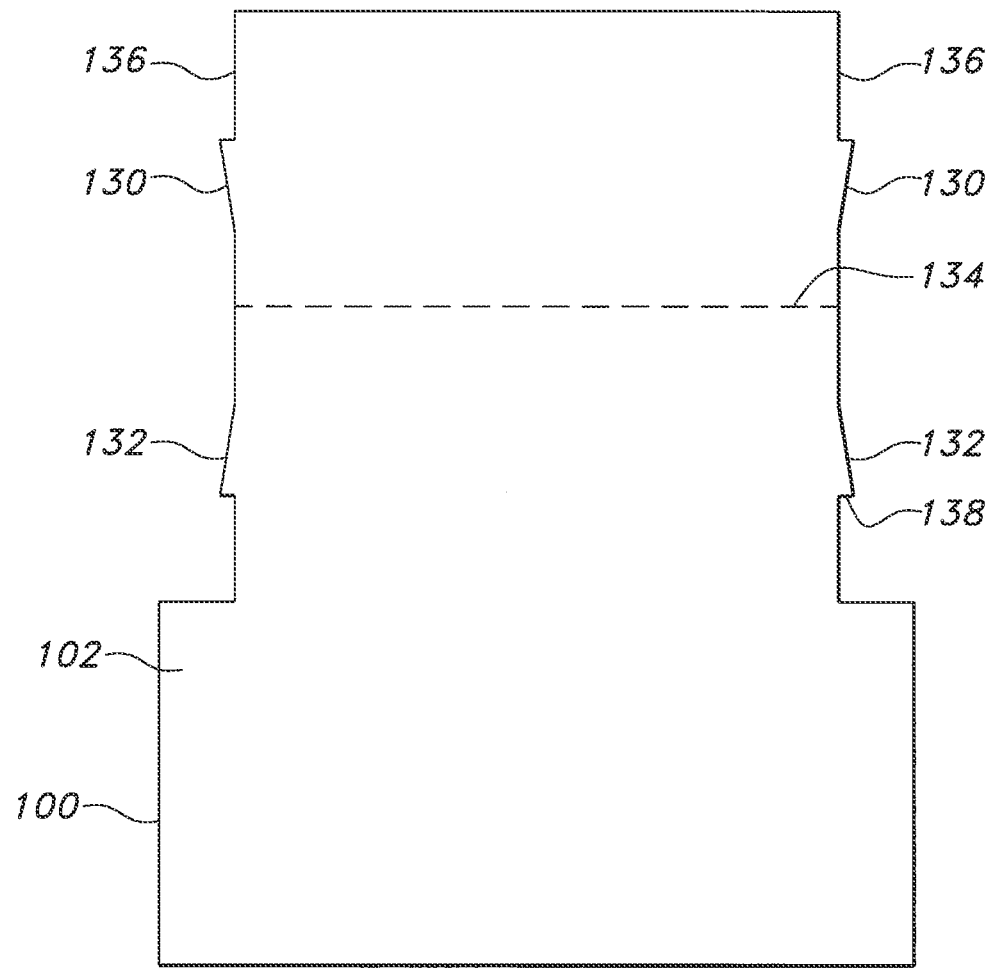

The draping system disclosed herein has a drape 100 made from a single piece of a first material 102 having an upper side or surface 104 (FIG. 2A) and a lower or underside or surface 106 (FIG. 2B) as shown generally in FIG. 2. The wider part of the drape 100 covers at least a portion of the lower tier 52 and the narrower part of the drape 100 covers at least a portion of the upper tire 54 when the drape 100 is installed on the table 50. The drape 100 may be folded along a fold line 134 so that the flares 130, 132 on the same side come together (FIG. 2C). After folding, the flares 130, 132 may be joined to each other by, for example, an adhesive, thus forming a pocket or envelope that may be slid over the upper tier during the donning procedure. The joined flares 130, 132 provide slightly more volume in the part of the pocket that is towards the rear of the upper tier after the narrow part of the drape is installed on the upper tier. This joined flare detail has been found to make the donning procedure surprisingly easier by reducing the resistance of the pocket with the upper tier. The maximum distance that the flare extends perpendicularly away from the side 136 is at the flare's widest point 138 and may be between 1 and 4 inches (2.5 to 10 cm), more particularly between 1.5 and 3 inches (3.25 and 7.5 cm) and more particularly about 2 inches (5 cm). FIG. 2C shows the flares 130, 132 taper into the drape toward the fold line 134 from its widest point 138. Other flare configurations are possible and envisioned, e.g. a tapering of material on both sides of the maximum distance.

The two tiered table is currently available in various widths (e.g., 4, 5 and 6 feet) and the drape is sized as is appropriate for the table on which it is to be used so that it covers the surfaces as described herein and as shown in the Figures. Note that in FIGS. 1, 3-5 the drape 100 is opaque, but the material 102 of the drape 100 can be transparent and/or translucent.

The drape may have a taper 118 as shown in FIG. 2 if desired, to help to eliminate excess fabric, for example, between the upper and lower tiers of the table. Excess fabric between the upper and lower tiers at the ends of the table can result in the excess fabric moving around and touching the draped surface of the lower tier, resulting in a non-sterile surface. A tapered drape also presents a neater appearance and helps avoid getting in the way of hospital personnel. Whether rectangular, tapered or having other modifications to its shape, it is important that the first material cover at least the table upper tier upper and lower surfaces, the front of the upper tier support posts and the lower tier upper surface. It is also important that the first material be impervious in order to maintain the sterile field on the upper surfaces where surgical items are placed.

In the discussions herein, coefficient of friction (COF) is a unit-less number that represents the static resistance to sliding of two surfaces in contact with each other. These values should be between 0 and 1. Higher values indicate more resistance to sliding. Generally, values over 0.50 are considered non-slip surfaces and values less than 0.20 are considered high-slip, when tested according to ASTM D1894-11e1, "Standard Test Method for Static and Kinetic Coefficients of Friction of Plastic Film and Sheeting".

There may be an area of a second material 108 having a higher coefficient of friction than the first material arranged on the upper side of the first material in an area that at least generally coincides with at least a portion of the upper surface of the lower tier of the table when the drape is installed on the table. The second material may, if desired, cover a larger area than merely the area corresponding to the upper surface of the lower tier of the table. The second material could cover the entire first material (e.g. as a laminate), for example, though this may be expensive. It is also desirable that the second material have a higher degree of absorbance than the first material so that liquids that may be spilled onto it during surgery would not run off onto the floor where they may become a hazard. During surgery, used instruments may be dropped or even tossed onto the table tiers, so it is helpful for the second (and third) material to cushion the landing, deter the instrument from sliding off the table, and absorb any liquids that may drip off of the instrument.

The second material 108 is desirably placed on the first material 102 such that it is on the upper surface of the lower tier 52 when the drape is installed on the table. It is placed on the upper side or surface 104 of the single piece material 102, meaning the second material 108 is not against the table when the drape is installed but is on the side of the single piece material 102 away from the table. The second material 108 should have a higher coefficient of friction than the single piece of first material 102, desirably greater than 0.50, so that items placed on it will be less likely to slide.

The drape 100 may have a third material 110 having a higher coefficient of friction than the first material 102 arranged on the upper side of the first material 102 in an area that generally coincides with at least a portion of the upper surface of the upper tier 54 of the table when the drape 100 is installed on the table, meaning the third material 110 is not against the table when the drape 100 is installed but is on the side of the single piece material 102 away from the table. The third material 108 should have a higher coefficient of friction than the single piece of first material 102, desirably greater than 0.50, so that items placed on it will be less likely to slide. It is also desirable that the third material have a higher degree of absorbance than the first material so that liquids that may be spilled onto it during surgery would not run off onto the floor where they may become a hazard.

The drape 100 may have a fourth material 112 having a higher coefficient of friction than the single piece of material 102, on the lower or under-side of the drape 100 in an area that generally coincides with at least a portion of the upper surface of the lower tier 52 of the table when the drape 100 is installed on the table, meaning the fourth material 112 is against the table when installed. As with the second material, the fourth material may, if desired, cover a larger area than merely the area corresponding to the upper surface of the lower tier of the table. The fourth material could cover the entire first material (e.g. as a laminate), for example, though this may be expensive. The fourth material has a COF desirably greater than 0.50.

Alternatively, the first material may be made from a film having a sufficiently high coefficient of friction that the drape will not slide off of a polished metal table surface as it is being installed. A single sheet drape having an impervious film with a nonwoven fabric on the upper surface and a high coefficient of friction lower surface, i.e., a COF desirably greater than 0.50, would be within the scope of this disclosure.

The drape 100 may have a fifth 114 material having a higher coefficient of friction than the single piece of material 102 on the lower or under-side of the drape 100 in an area that generally coincides with at least a portion of the upper surface of the upper tier 54 of the table when the drape 100 is installed on the table, meaning the fifth material 114 is against the table when installed. The fifth material has a COF desirably greater than 0.50.

The single piece of a first material 102 is desirably an impervious film, though it may be other materials such as wax coated paper and laminates including films. It is also desirable, though not required, that the first material be clear. The first material has a COF generally less than 0.50, more particularly less than 0.40, still more particularly less than 0.30 and even more particularly less than 0.20 on the side against the table when the drape is installed on the table. The first material desirably has a thickness between about 0.3 and 4 mils (7.6 to 127 micron), more desirably between 1.5 and 3 mils (38 and 76 microns). The first material may be a film made from a polyolefin like polyethylene and polypropylene, and may be a multilayer film having layers with different compositions and properties made according to known methods such as co-extrusion.

The second material 108 and third material 110 may be the same type of material as each other, though they may also be different from each other. These materials serve as a surface onto which may be placed surgical items like instrument trays, single instruments and the like and so they are desirably placed on the first material 102 as a continuous layer. Alternatively, the second 108 and third 110 materials may be placed in a discontinuous pattern. The second 108 and third 110 materials may be in shapes, for example, that suggest the shapes of particular objects to be placed on them so that the objects are placed in a desired predetermined location for surgery. Other indicia such as pictures or words may be used to indicate desired predetermined locations for particular surgical items.

The surgical items may be smooth and may slide if the table is bumped or the tier is not horizontal. The second 108 and third 110 materials should have a higher coefficient of friction than the single piece of a first material 102 to aid in maintaining the items in a stable position without movement. The second and third materials desirably have a COF generally greater than 0.50, more particularly greater than 0.60, still more particularly greater than 0.70. As discussed above, it is also helpful for the second and third materials to cushion the tiers and absorb liquid. Exemplary materials for this purpose include nonwoven fabrics and webs, foams and multilayer laminates thereof. While normally made from polymers that are not wettable, nonwoven fabrics and foams may be made wettable through the use of additives or post formation surface treatments, thus increasing their liquid absorbance. Foams for this service are desirably open celled to provide more open volume for liquid entrapment.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein "multilayer nonwoven laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc.

The fourth 112 material and fifth material 114 may be the same as each other, though they may also be different from each other. The fourth 112 and fifth 114 materials may be placed as a continuum on the lower or under-side of the first material 102 or may be placed and attached in strips or in any other discontinuous pattern as desired. These materials provide a higher coefficient of friction surface on the underside of the single piece of material 102 so that the drape 100 doesn't slide off of the table as it is being installed. The table is generally highly polished and is slippery for polymer materials. Placing a film, generally having a very low coefficient of friction, onto the table and unfolding the film to install it can result in considerable movement of the drape. This can even result in the drape slipping off the table onto the floor. If this occurs the drape can no longer be considered sterile and must be replaced, costing money and using time. The fourth and fifth materials have a COF generally greater than 0.50, more particularly greater than 0.60, still more particularly greater than 0.70 and even more particularly greater than 0.80.

Exemplary materials for the fourth 112 and fifth 114 materials include hot melt adhesives, nonwoven fabrics with tackifying agents, and foams and films having high coefficients of friction. It has been found that films made from metallocene polymers have a relatively high COF and such films and laminates of these films with foams and nonwoven fabrics may be used.

Meltblown fibers, for example, may be made from an elastomeric polymer that may be tacky when formed into fibers or, alternatively, a compatible tackifying resin may be added to an extrudable elastomeric composition to provide tackified fibers. Tackifying resins and tackified extrudable elastomeric compositions as disclosed in U.S. Pat. No. 4,787,699, hereby incorporated by reference, are suitable.

Any tackifier resin can be used that is compatible with the polymers used and can withstand the high processing (e.g., extrusion) temperatures. If the polymer (e.g., elastomeric block copolymer) is blended with processing aids such as, for example, polyolefins or extending oils, the tackifier resin should also be compatible with those processing aids. Generally, hydrogenated hydrocarbon resins are preferred tackifying resins, because of their better temperature stability. Other tackifying resins which are compatible with the other components of the composition and can withstand the high processing temperatures can also be used.

The drape 100 described above may be held in place on the table using a continuous band 120 that encircles the upper portion of the table width-wise end to end, i.e. in the longest horizontal dimension as shown in FIG. 1. Band 120 is made from or with elastomeric material so that it stretches and at least partial retracts after being stretched. The continuous band 120 should encircle the upper tier 54 at the rear of the tier 54 or on the upper part of the support posts 56. As may be seen from FIG. 1, the continuous band 120 holds the drape 100 above the lower tier 52 without allowing appreciable sag towards the ends of the table.

Figure 3:
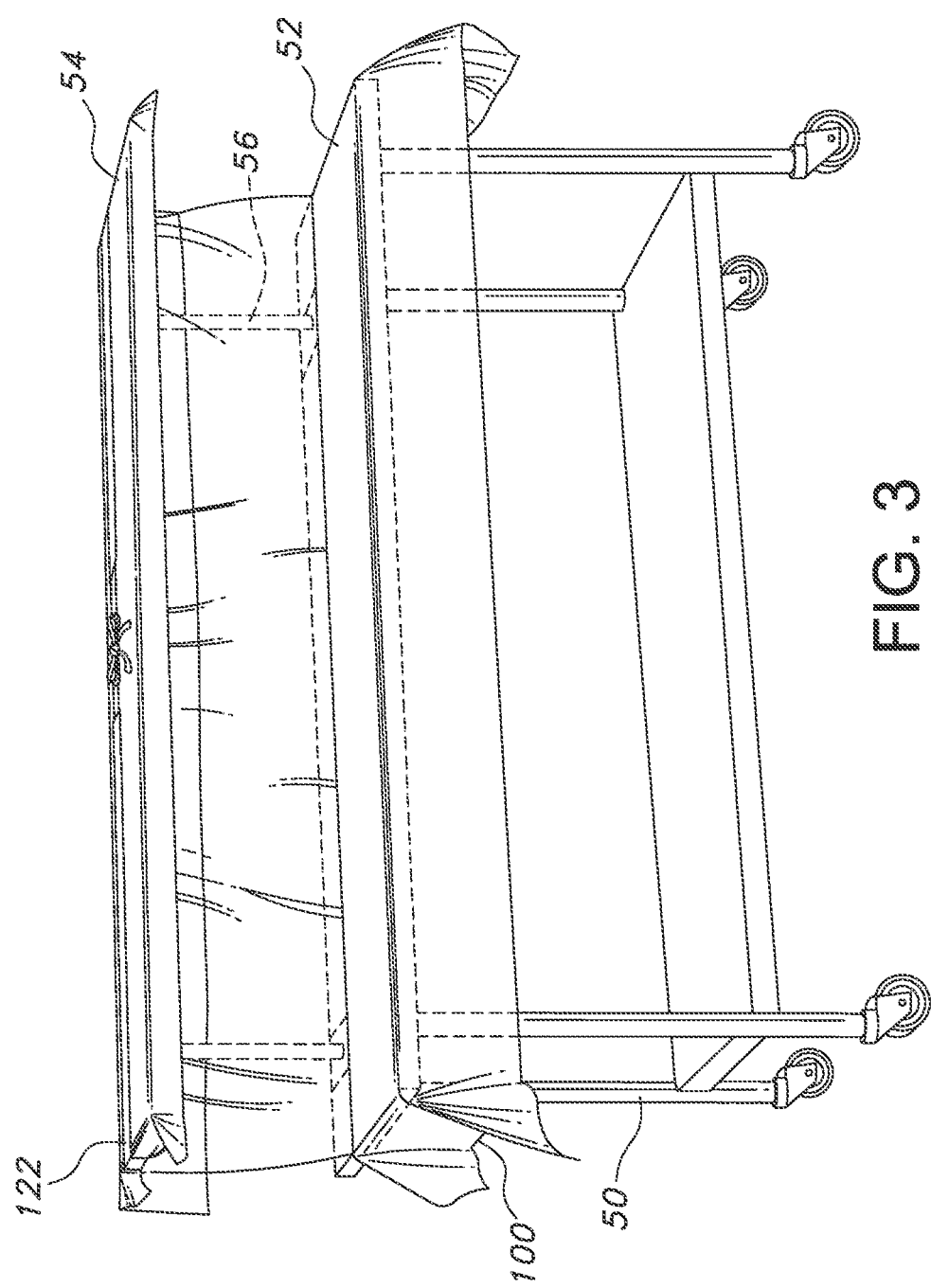
FIG. 3 is a perspective view of a surgical instrument table covered with the surgical sterile drape and held in place with a discontinuous band of material encircling the upper tier from end to end and tied together.

Alternatively, the band may be discontinuous and may be elastic, non-elastic, or may have elastic and non-elastic portions. The discontinuous band 122 may at least partially encircle the upper tier 54 at the rear or the upper part of the support posts 56 in the same manner as the continuous band 120 described above. The discontinuous band 122 may be attached to itself, using the band ends 124, by known fastening means such as by tying the ends together in a knot or releasable bow (e.g. like shoe laces) as shown in FIG. 3, by using adhesive on one or both ends, by using a hook fastener on one end and loop on the other, by stapling, by taping or by other known means.

Figure 4:
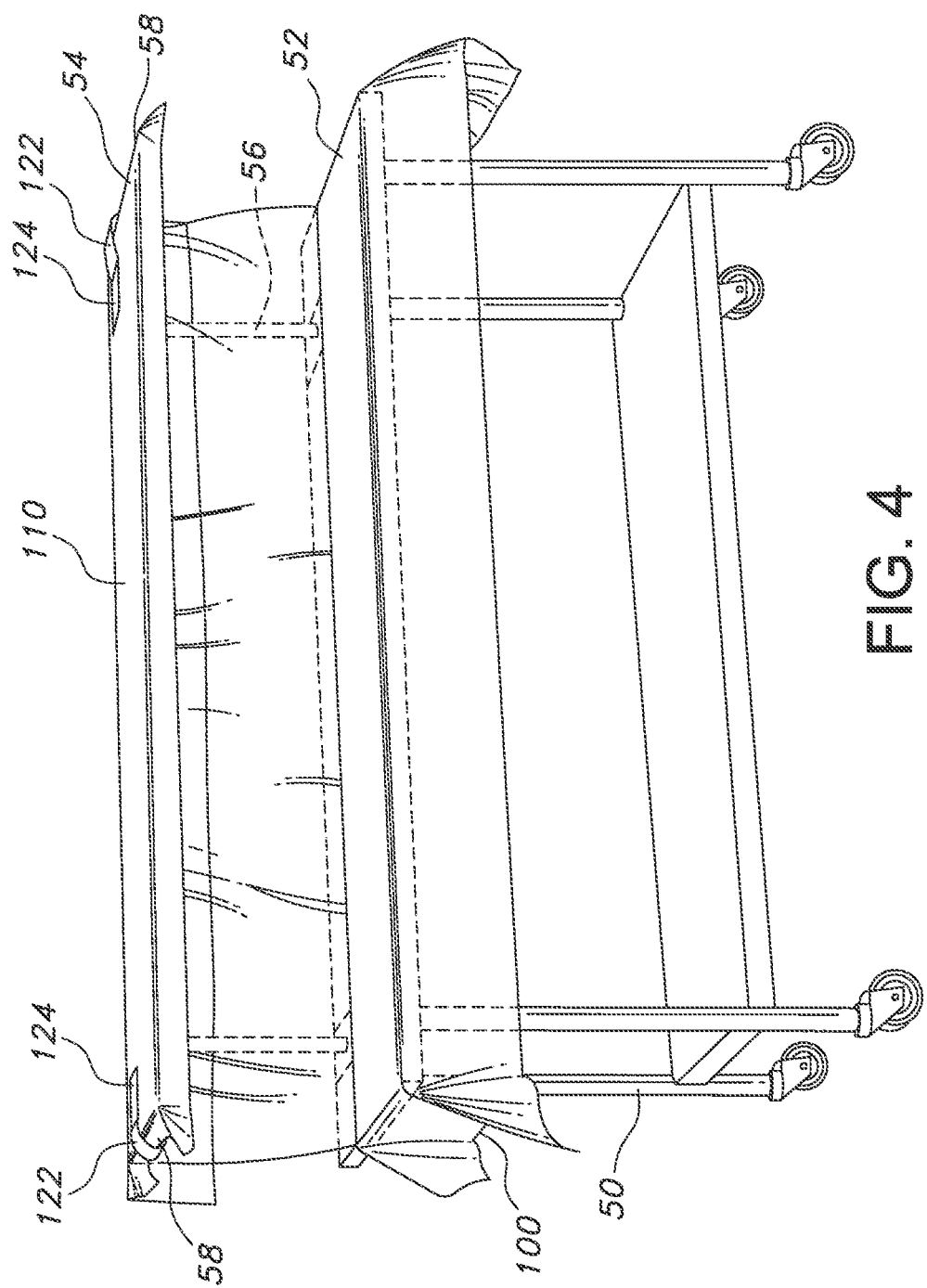
FIG. 4 is a perspective view of a surgical instrument table covered with the surgical sterile drape and held in place with a discontinuous band of material across the lower side of the upper tier from end to end, which then loops around to the top of the upper tier where it attaches to the upper surface of the drape with hook and loop fastening.
Figure 5:
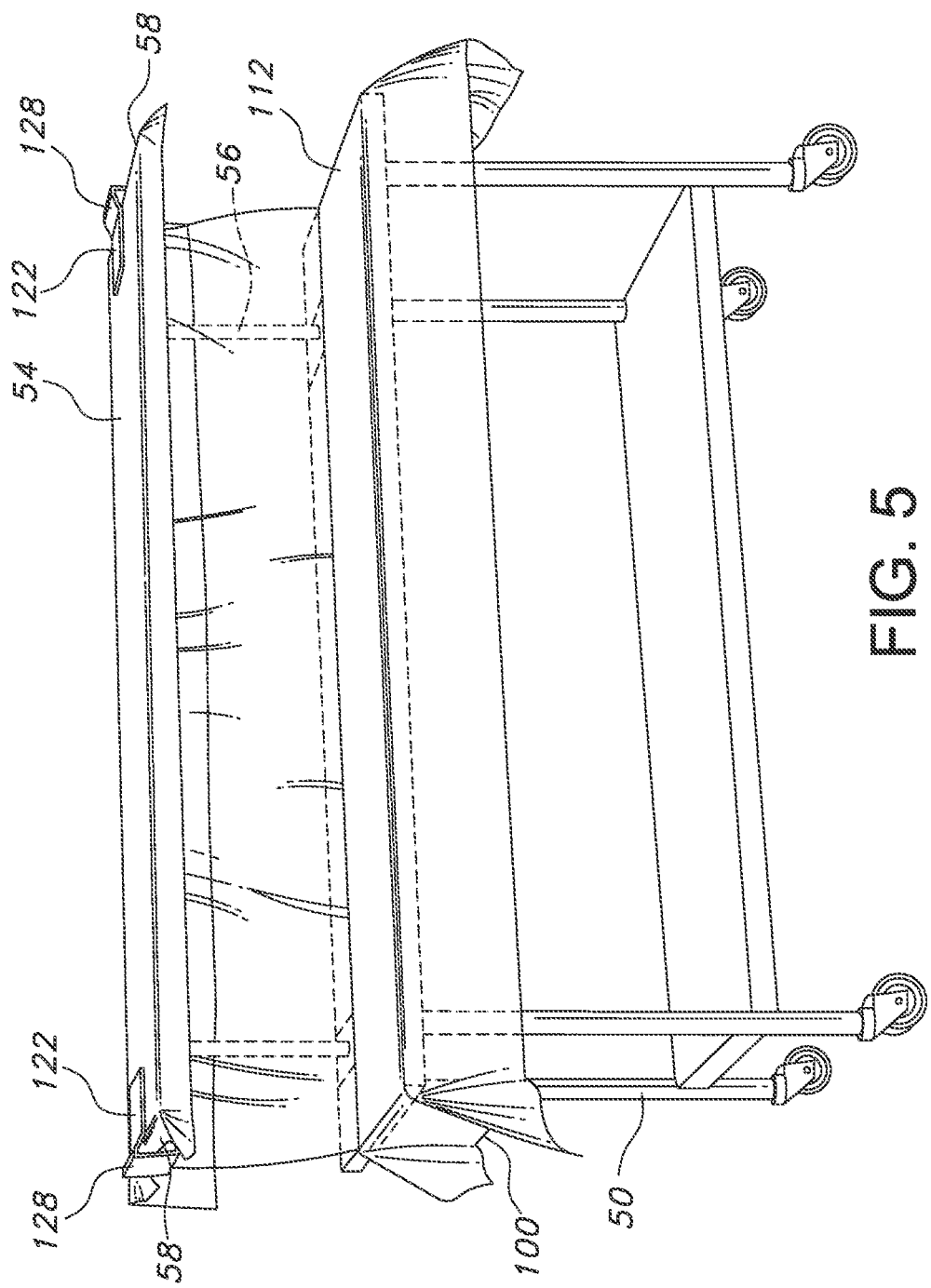
FIG. 5 is a perspective view of a surgical instrument table covered with the surgical sterile drape and held in place with a discontinuous band of material across the lower side of the upper tier from end to end and held in place with clamps.

Instead of attaching the discontinuous band 122 to itself at the ends 124, the discontinuous band 122 may also be equipped with hook type fasteners 126 on either end 124 of the band 122 and the hook fasteners 126 attached to the third material 110 when the third material 110 is a loop type material, with the band 122 running below the upper tier 54 and looping around to the top of the upper tier 54 upon reaching the ends, as shown in FIG. 4. The discontinuous band 122 may also be held in place on either end of the table on the upper tier 54 or on the upper part of the posts 56 by, for example, using clamps 128 as shown in FIG. 5. The clamps may be spring loaded or screwed in place, or clamped in place by other means as is known. The clamps can be used to hold each end of the discontinuous band 122 firmly against either end 58 of the table, with the discontinuous band 122 running below the upper tier 54.

The band, whether continuous or discontinuous, may have a width, depending on the strength of the material from which the band is made, from a millimeter to a width equal to the depth of the upper tier, more desirably between 3 and 100 mm, still more desirably between 5 and 30 mm. The band, whether continuous or discontinuous, holds the drape 100 above the lower tier 52 without allowing appreciable sag towards the ends of the table.

As used herein and in the claims, the term "comprising" is inclusive or open-ended and does not exclude additional unrecited elements, compositional components, or method steps.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A draping system for a surgical table having an upper tier and a lower tier, each tier having an upper surface, a lower surface, and a front and rear, the table having support posts between the upper tier and the lower tier to support the upper tier, the system comprising: a drape capable of being placed on the upper tier and the lower tier of said surgical table, where said drape is made from a single piece of first material having an upper and lower side, with an area of a second material having a higher coefficient of friction than said first material arranged on the upper side of said first material in an area that at least generally coincides with the upper surface of the lower tier of the table when said drape is installed on said table, and a band adapted to hold said drape in place at the rear of the upper tier of the table when said drape is installed on said table, wherein the band has an end to end dimension at least as long as a longest horizontal dimension of said drape, wherein the band is a continuous band or a discontinuous band, wherein the continuous band is a continuous loop that is configured to completely encircle both the upper surface and lower surface of the upper tier of the table and the discontinuous band is a single band with two ends configured to releasably attach at and partially encircle the upper surface and completely encircle the lower surface of the upper tier of the table.

2. The draping system of claim 1, the drape further comprising a third material having a higher coefficient of friction than said first material arranged on a portion of the upper side of the first material in an area that is adapted to generally coincide with a portion of the upper surface of the upper tier of the table when said drape is installed on said table.

3. The draping system of claim 2, the drape further comprising a fourth material having a high coefficient of friction on a portion of the lower side of said drape in an area that is adapted to generally coincide with a portion of the upper surface of the lower tier of the table.

4. The draping system of claim 3, the drape further comprising a fifth material having a high coefficient of friction on a portion of the lower side of said drape in an area that is adapted to generally coincide with at least a portion of the upper surface of the upper tier of the table.

5. The draping system of claim 3 wherein said fourth material, fifth material, or a combination thereof on said lower side of said drape is a hot melt adhesive.

6. The draping system of claim 1, wherein said drape comprises a film.

7. The draping system of claim 6, wherein said film is clear.

8. The draping system of claim 1, wherein said drape is free of a fastener in a center of the drape to attach the drape to the table.

9. The draping system of claim 1 wherein said continuous band is elastic.

10. The draping system of claim 1 wherein said band is said discontinuous band.

11. The draping system of claim 1 wherein said band is said discontinuous band and attaches to itself.

12. The draping system of claim 1 wherein said band is said discontinuous band and attaches to a third material.

13. The draping system of claim 1, wherein the band is said discontinuous band, and further comprises comprising a first clamp and a second clamp, wherein the first clamp is adapted to hold the band in place at a first end of said table and the second clamp is adapted to hold the band in place at a second end of said table.

14. The draping system of claim 1 wherein said drape is adapted to be tapered between the upper and lower tiers of the table.

15. A draping system for a surgical table having an upper tier and a lower tier, the upper tier supported by support posts, each tier having an upper surface, a lower surface, and a front and rear, comprising: a drape capable of being placed on the upper tier and the lower tier of said surgical table, where said drape is made from a single piece of impervious film having an upper and lower side, with an area of a wettable nonwoven fabric having a higher coefficient of friction than said film arranged on the upper side of the film in an area that generally coincides with the upper surface of the lower tier of the table when said drape is installed on said table, and a continuous or discontinuous band adapted to hold said drape in place at the rear of the upper tier of the table when said drape is installed on said table, wherein the continuous or discontinuous band has an end to end dimension at least as long as a longest horizontal dimension of said drape, wherein the continuous band is a continuous loop, that is configured to completely encircle both the upper surface and lower surface of the upper tier of the table and the discontinuous band is a single band with two ends configured to releasably attach at and partially encircle the upper surface of the upper tier of the table and completely encircles the lower surface of the upper tier of the table.

16. The draping system of claim 15 further comprising a material having a high coefficient of friction on a portion of the lower side of said drape in an area that is adapted to generally coincide with a portion of the upper surface of the lower tier of the table.

* * * * *